United States Patent
Kamiya et al.

(10) Patent No.: US 12,016,676 B2
(45) Date of Patent: Jun. 25, 2024

(54) MANAGEMENT DEVICE FOR ASSISTIVE DEVICE AND MANAGEMENT METHOD

(71) Applicant: FUJI CORPORATION, Aichi-ken (JP)

(72) Inventors: Yuki Kamiya, Toyoake (JP); Ryu Takahashi, Toyota (JP); Satoshi Shimizu, Chiryu (JP); Takehiro Hiraoka, Chiryu (JP); Takahiro Katsuki, Aichi-ken (JP)

(73) Assignee: FUJI CORPORATION, Aichi-ken (JP)

( * ) Notice: Subject to any disclaimer, the term of this patent is extended or adjusted under 35 U.S.C. 154(b) by 529 days.

(21) Appl. No.: 15/734,562

(22) PCT Filed: Jun. 5, 2018

(86) PCT No.: PCT/JP2018/021617
§ 371 (c)(1),
(2) Date: Dec. 3, 2020

(87) PCT Pub. No.: WO2019/234838
PCT Pub. Date: Dec. 12, 2019

(65) Prior Publication Data
US 2021/0228110 A1    Jul. 29, 2021

(51) Int. Cl.
*A61G 7/10*    (2006.01)
*A61B 5/11*    (2006.01)
(Continued)

(52) U.S. Cl.
CPC .......... *A61B 5/1116* (2013.01); *A61G 7/1007* (2013.01); *A61G 7/1046* (2013.01);
(Continued)

(58) Field of Classification Search
CPC ........ A61B 2505/09; A61B 2562/0252; A61B 5/1112; A61B 5/1116; A61G 2203/30;
(Continued)

(56) References Cited

U.S. PATENT DOCUMENTS

2002/0193709 A1*  12/2002  Bolze ............... A61B 17/22029
                                                          601/4
2017/0049658 A1*   2/2017  Kim ......................... A61H 3/00
(Continued)

FOREIGN PATENT DOCUMENTS

CN    103905871    7/2014
CN    106420269    2/2017
(Continued)

OTHER PUBLICATIONS

"International Search Report (Form PCT/ISA/210) of PCT/JP2018/021617," mailed on Aug. 28, 2018, with English translation thereof, pp. 1-2.

*Primary Examiner* — Mohamed Charioui
*Assistant Examiner* — Christine Y Liao
(74) *Attorney, Agent, or Firm* — JCIPRNET

(57) ABSTRACT

A management device is used in an assistive device configured to assist an erecting action and a seating action of a care receiver and records, as a log data, an action history including erecting actions and seating actions. The management device for the assistive device includes a detecting section for detecting, in the log data, a cycle action executed in the order of the erecting action and then the seating action, and a determination section for determining, based on the log data, whether the cycle action detected is a transfer action in which the care receiver is transferred.

11 Claims, 4 Drawing Sheets

(51) Int. Cl.
*A61H 3/04* (2006.01)
*G16H 20/30* (2018.01)

(52) U.S. Cl.
CPC .............. *A61H 3/04* (2013.01); *G16H 20/30* (2018.01); *A61B 2562/0252* (2013.01); *A61G 2203/42* (2013.01); *A61H 2201/5064* (2013.01); *A61H 2201/5069* (2013.01)

(58) Field of Classification Search
CPC ............ A61G 2203/32; A61G 2203/42; A61G 7/1007; A61G 7/1017; A61G 7/1019; A61G 7/1046; A61G 7/1048; A61G 7/1065; A61H 2201/5064; A61H 2201/5069; A61H 3/04; G16H 20/03
See application file for complete search history.

(56) References Cited

U.S. PATENT DOCUMENTS

2017/0128291 A1\* 5/2017 Kim .................. A61H 3/00
2018/0214330 A1\* 8/2018 Cooper ............. A61G 5/1075

FOREIGN PATENT DOCUMENTS

| JP | 2008073501 | 4/2008 |
| JP | 2016519599 | 7/2016 |
| WO | 2018051405 | 3/2018 |

\* cited by examiner

[Fig. 1]
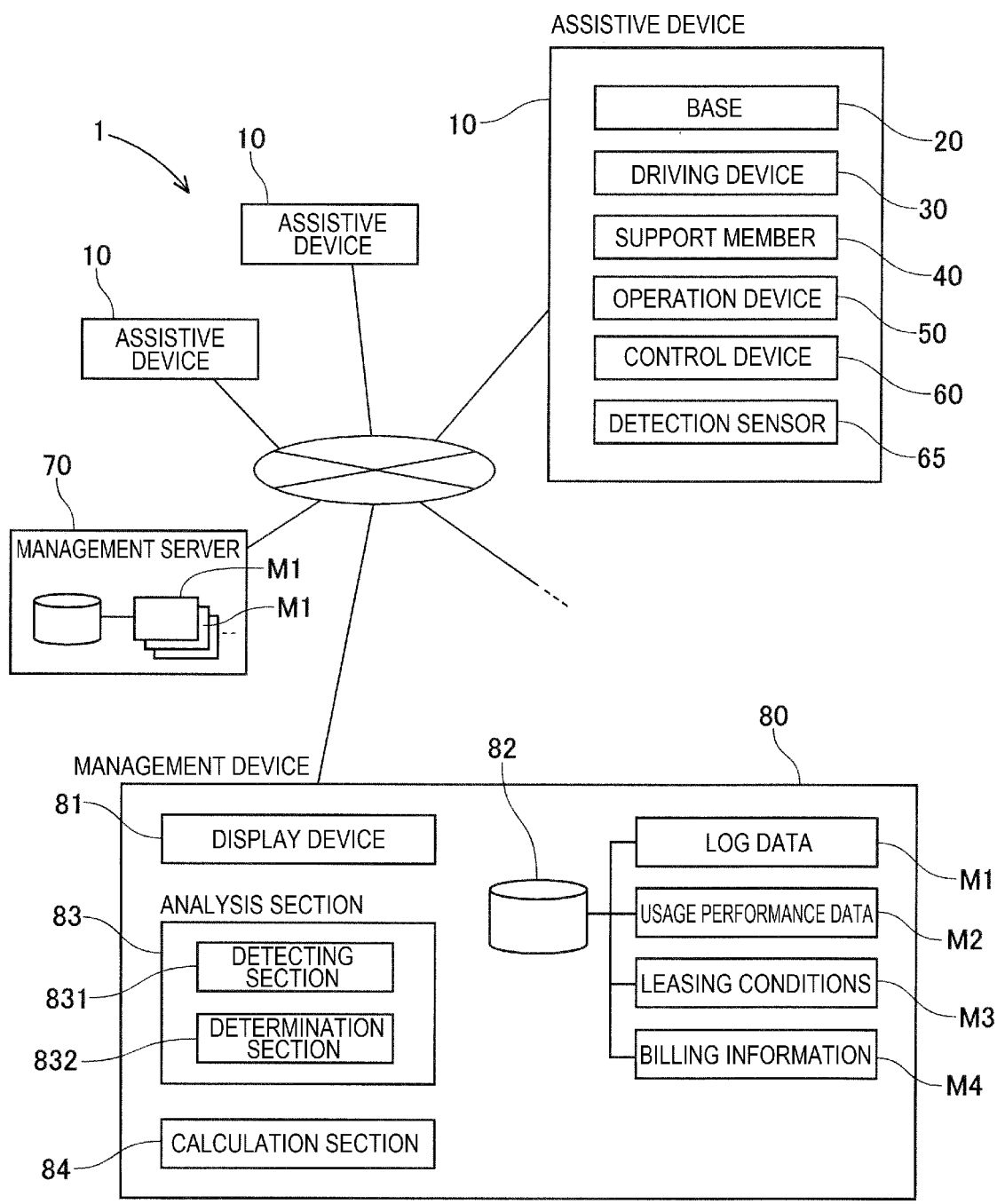

[Fig. 2]
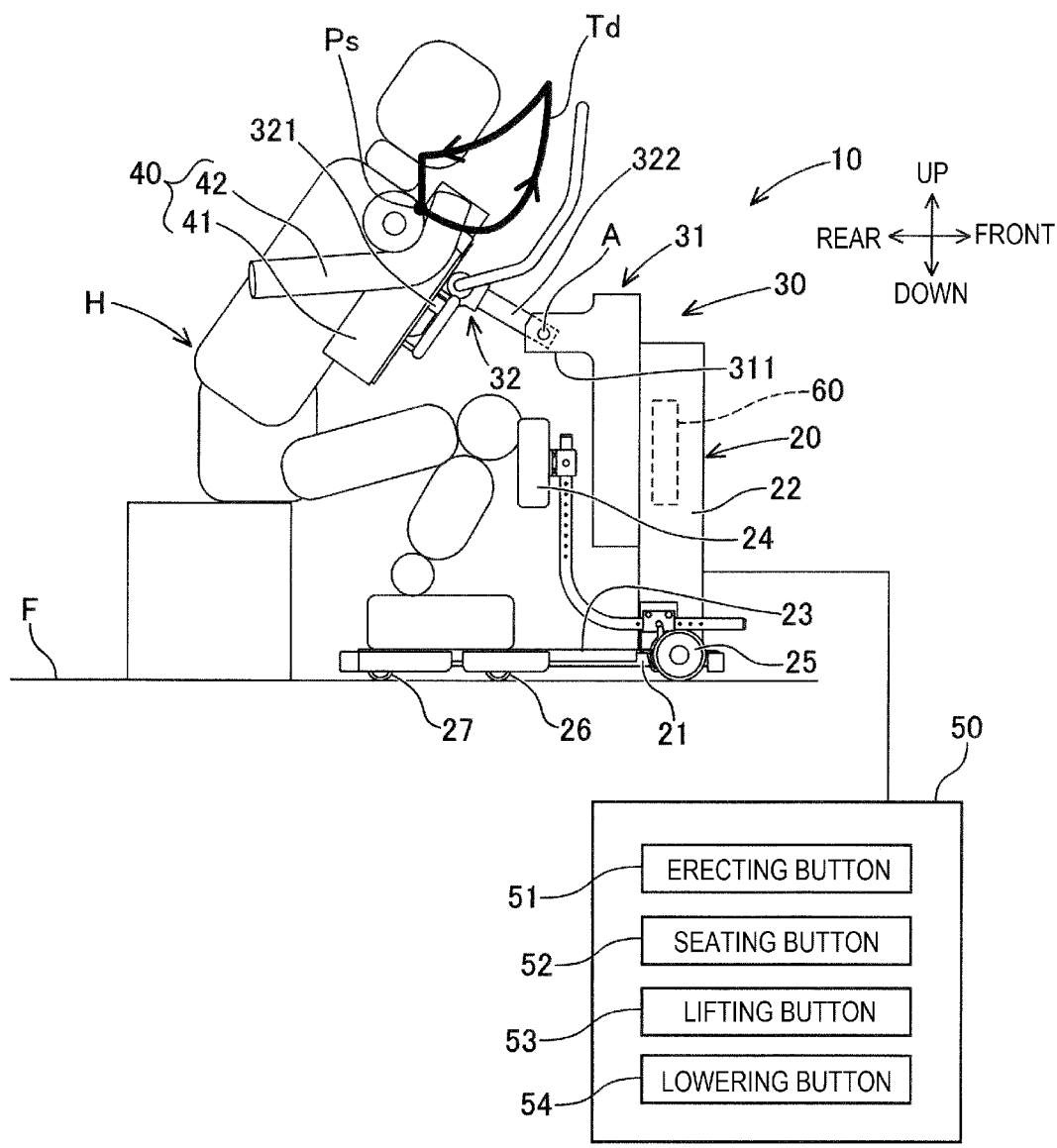

[Fig. 3]

LOG DATA M1  ASSISTIVE DEVICE: ID(Fh16xx)

| No | OPERATION HISTORY | | | ACTION HISTORY | | | | STATE OF ASSISTIVE DEVICE | | | IDENTIFICATION INFORMATION |
|---|---|---|---|---|---|---|---|---|---|---|---|
| | OPERATION | START TIME | END TIME | ACTION | START TIME | END TIME | EXECUTION TIME | LIFTING AND LOWERING SECTION | SWING SECTION | ‥ | CAREGIVER / CARE RECEIVER |
| N11 | SEATING | h: m: s | h: m: s | SEATING | h: m: s | h: m: s | m: s | Z11 | Ang11 | ‥ | A11/ H11 |
| : | : | : | : | : | : | : | : | : | : | : | |
| N21 | LIFTING | h: m: s | h: m: s | – | – | – | – | Z21 | Ang21 | ‥ | A21/ H21 |
| : | : | : | : | : | : | : | : | : | : | : | |
| N31 | ERECTING | h: m: s | h: m: s | ERECTING | h: m: s | h: m: s | m: s | Z31 | Ang31 | ‥ | |
| N32 | SEATING | h: m: s | h: m: s | SEATING | h: m: s | h: m: s | m: s | Z32 | Ang32 | ‥ | |
| : | : | : | : | : | : | : | : | : | : | : | |
| N39 | LOWERING | h: m: s | h: m: s | LOWERING | h: m: s | h: m: s | m: s | Z39 | Ang39 | ‥ | |
| : | : | : | : | : | : | : | : | : | : | : | |
| N41 | LIFTING | h: m: s | h: m: s | LIFTING | h: m: s | h: m: s | m: s | Z41 | Ang41 | ‥ | A31/ H31 |
| : | : | : | : | : | : | : | : | : | : | : | |

[Fig. 4]

USAGE PERIOD:
USAGE PERFORMANCE DATA M2   m1/d1-m2/d2

| NUMBER OF USES (NUMBER OF EXECUTIONS) | N11 TIMES |
|---|---|
| USAGE TIME (TIME REQUIRED) | h1 : m1 : s1 |

[Fig. 5]

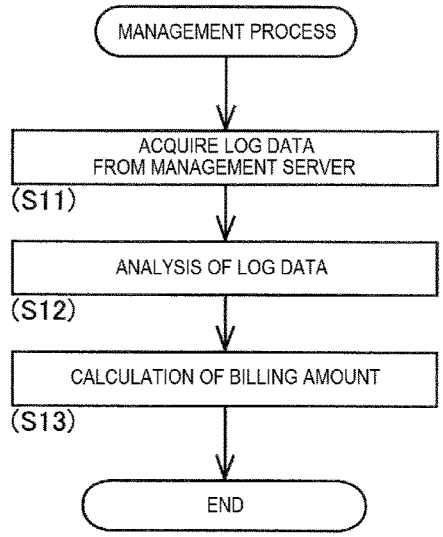

[Fig. 6]
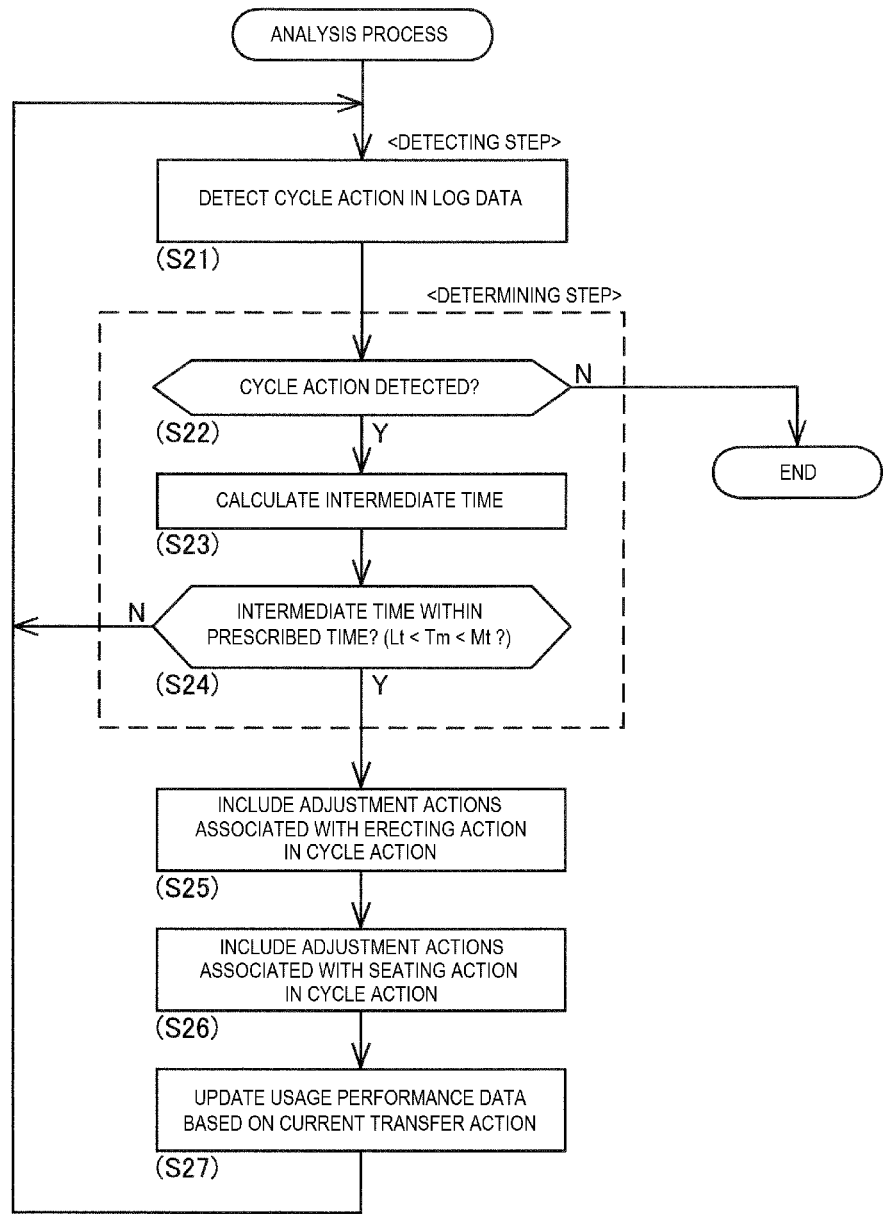

MANAGEMENT DEVICE FOR ASSISTIVE DEVICE AND MANAGEMENT METHOD

CROSS-REFERENCE TO RELATED APPLICATION

This application is a 371 application of the international PCT application serial no. PCT/JP2018/021617, filed on Jun. 5, 2018. The entirety of the above-mentioned patent application is hereby incorporated by reference herein and made a part of this specification.

TECHNICAL FIELD

The present disclosure relates to a management device for an assistive device and a management method.

BACKGROUND ART

Patent Literature 1 discloses an assistive device configured to assist a transfer action of a care receiver. In assisting the transfer action, the assistive device performs a directional change after an erecting action of lifting the buttocks of the care receiver in a sitting posture from a seating surface is completed, and performs a seating action of lowering the buttocks of the care receiver to a seat. As a result, the care receiver is transferred from a bed to a wheelchair, for example. Some assistive devices record actions of the assistive device as log data in order to analyze each action by tracing and the like.

PATENT LITERATURE

Patent Literature 1: JP-A-2008-073501

SUMMARY OF THE DISCLOSURE

Technical Problem

The assistive device may, for example, be made to perform actions unrelated to the transfer action such as a test run to check the action of each section. If this is done, the actions described above will be recorded in the log data and may be erroneously regarded as a transfer action during analysis. This may reduce the accuracy of analyses such as tracing.

It is an object of the present specification to provide a management device and a management method for an assistive device capable of detecting a transfer action in log data and improving the accuracy of analysis using log data.

Solution to Problem

The present specification discloses a management device for an assistive device configured to assist the erecting action and seating action of a care receiver and record an action history including the erecting actions and seating actions as log data; the management device comprising: a detecting section configured to detect in the log data a cycle action executed in the order of an erecting action and a seating action; and a determination section configured to determine based on the log data whether the detected cycle action is a transfer action in which the care receiver was transferred.

The present specification discloses a management method for an assistive device configured to assist the erecting action and seating action of a care receiver and record an action history including the erecting actions and seating actions as log data; the assistive device comprising: a detecting step for detecting in the log data a cycle action executed in the order of an erecting action and a seating action; and a determining step for determining based on the log data whether the detected cycle action is a transfer action in which the care receiver was transferred.

Advantageous Effect of the Disclosure

Since it is determined whether a cycle action in the log data is a transfer action, with such a configuration for a management device and a management method for an assistive device, it is possible to more accurately detect the transfer action in the log data. As a result, the accuracy of analysis using log data is improved.

BRIEF DESCRIPTION OF DRAWINGS

FIG. 1 A schematic diagram showing an assistive system of an embodiment including a management device for an assistive device.

FIG. 2 A side view showing an assistive device for supporting a care receiver in a sitting posture.

FIG. 3 A diagram showing log data recorded by the assistive device.

FIG. 4 A diagram showing usage performance data.

FIG. 5 A flowchart showing a management process of the assistive device performed by a management device.

FIG. 6 A flowchart showing a log data analysis process in the management process of FIG. 5.

DESCRIPTION OF EMBODIMENTS

1. Configuration of the Assistive System

An embodiment of a management device and a management method of an assistive device will be described below with reference to the drawings. Assistive system 1 supervises one or more assistive devices 10. As shown in FIG. 1, assistive system 1 includes assistive device 10, management server 70, and management device 80. Assistive device 10 and management device 80 are communicably connected to management server 70 via the internet.

2. Configuration of Assistive Device 10

Assistive device 10 assists care receiver H (refer to FIG. 2) in an erecting action from a sitting posture to a standing posture and assists a sitting action from the standing posture to the sitting posture. Since assistive device 10 supports the upper body of care receiver H in the standing posture, one caregiver can tow and, for example, move assistive device 10 to a target location in an assistance facility.

The "standing posture" of care receiver H refers to a posture in which the lower body of care receiver H is erected but the upper body may be in any position. In other words, the erecting action of care receiver H refers to an action of lifting the buttocks of care receiver H into the standing posture. The seating action of care receiver H refers to an action of lowering the buttocks of care receiver H into a sitting posture.

Assistive device 10 includes base 20, driving device 30, support member 40, operation device 50, and control device 60, as shown in FIGS. 1 and 2. Base 20 includes frame 21, support column 22, footrest 23, lower leg contact 24, six wheels 25 to 27, and the like. Frame 21 is provided substantially horizontally near floor F. Support column 22 is fixed to frame 21 while extending upward from the center in the left-right direction of the front of frame 21. Support column 22 may be provided so as to be perpendicular to floor For at a predetermined angle in the front-rear direction.

Footrest 23 is fixed to the rear of the upper face of frame 21 so as to be horizontal. Lower leg contact 24 is fixed to support column 22 so as to be positioned above footrest 23. Lower leg contact 24 has a cushion member at a point at which the lower leg of care receiver H comes into contact. On the underside of frame 21, three wheels 25 to 27 are provided to both the left and right sides. Each wheel 25 to 27 has a steering function to change the direction of movement. With the steering function of six wheels 25 to 27, assistive device 10 is not only capable of moving forward and backward and changing direction but also moving sideways and spinning in place.

Driving device 30 supports support member 40 so that support member is movable in the up-down direction and the front-rear direction of base 20, support member 40 being for supporting the upper body of care receiver H. In the present embodiment, driving device 30 includes lifting and lowering section 31 and swing section 32. Driving device 30 is controlled by control device 60 so as to operate lifting and lowering section 31 and swing section 32. Driving device 30 is configured to move support member 40 along a predetermined movement trajectory by coordination of the up-down movement of lifting and lowering section 31 and rotation of swing section 32.

Lifting and lowering section 31 moves linearly in the up-down direction with respect to base 20. Lifting and lowering section 31 has a long elongated shape in the up-down direction and is guided by a guide (not shown) of the rear face of support column 22. Lifting and lowering section 31 moves up and down along the guide of support column 22 by the driving of a linear motion device (not shown). Inside lifting and lowering section 31, a motor for pivoting swing section 32 (not shown) is accommodated. Lifting and lowering section 31 has swing support section 311. Swing support section 311 rotatably supports swing section 32 around central axis A.

Swing section 32 rotates around central axis A provided in lifting and lowering section 31 and causes support member 40 to swing. Swing section 32 includes swing main body 321 and arm 322. Swing main body 321 is an attachment portion for attaching and detaching support member 40. Arm 322 is integrally fixed to swing main body 321. One end of arm 322 is rotatably supported around central axis A of swing support section 311 of lifting and lowering section 31.

Arm 322 is rotated by the driving of the motor. When assistive device 10 assists the erecting action, arm 322 is mainly pivoted forward from a state extending rearward. On the other hand, when assistive device 10 assists the seating action, arm 322 is mainly pivoted rearward so as to extend rearward. With the above configuration, swing section 32 is pivoted about a horizontal axis (central axis A) parallel to the left-right direction of base 20 and swings support member 40 attached to swing main body 321 at the distal end of arm 322.

Support member 40 is a member for supporting the upper body of care receiver H. Support member 40 includes trunk support section 41 and a pair of side support sections 42. Trunk support section 41 has a planar shape similar to the trunk shape of care receiver H and can be flexibly deformed. The support surface of trunk support section 41 is in surface contact with the front surface of the trunk of the upper body of care receiver H and supports the trunk. More specifically, the supporting surface of trunk support section 41 supports care receiver H from below in a range from the chest to the abdomen. Further, trunk support section 41 is attached to swing main body 321.

The pair of side support sections 42 are supported by trunk support section 41 and support the sides of care receiver H. More specifically, the pair of side support sections 42 are provided on the right and left sides of trunk support section 41. Side support sections 42 are swingably supported by trunk support section 41. Side support sections 42 are rod-shaped members having an L-shape. The surface of side support sections 42 is covered by a material that can be flexibly deformed.

Operation device 50 has multiple buttons corresponding to each action assisted by assistive device 10. In the present embodiment, operation device 50 has erecting button 51, seating button 52, lifting button 53, and lowering button 54 corresponding to the order of the erecting action, the seating action, the lifting action, and the lowering action. Operation device 50 described above is connected to control device 60 via, for example, a telescopic signal cable. When any button of operation device 50 is pressed, a signal corresponding to the type of the button is sent to control device 60 while the button is depressed.

The "lifting action" is an action of lifting the upper body of care receiver H while maintaining the current angle of the upper body of care receiver H. The "lowering action" is an action of lowering the upper body of care receiver H while maintaining the current angle of the upper body of care receiver H. In the lifting and lowering actions, support member 40 does not pivot about central axis A.

Control device 60 controls the action of lifting and lowering section 31 and swing section 32 of driving device 30. In the action process for assisting the erecting action and the seating action of care receiver H, control device 60 activates lifting and lowering section 31 and swing section 32 based on the operation of operation device 50. When performing the erecting action and the seating action, control device 60 controls the movement of support member 40 by coordinating the up-down movement of lifting and lowering section 31 and the rotation of swing section 32.

Control device 60 records log data M1 that enables actions of assistive device 10 to be traced. "Log data M1" includes at least one of an action history of various actions including the erecting action and the seating action, and an operation history of various operations for which executions of various actions are requested. In the present embodiment, as shown in FIG. 3, log data M1 includes an operation history, an action history, states of the assistive device, and identification information. The "operation history" shows the content of the operation and the start time and end time of the operation of operation device 50.

The "action history" includes the start time and the end time of the action of driving device 30 actually controlled by control device 60 in response to various operations on operation device 50, and the execution time which is equal to the difference between the start time and the end time. Here, control device 60 controls so that driving device 30 operates only while any button of operation device 50 is depressed. Therefore, the operation history and the action history substantially coincide with each other. However, the operation history and the action history do not coincide with each other when control device 60 executes a cancellation process.

More specifically, when a predetermined action is being executed or when the position of a movable section (lifting and lowering section 31 and swinging section 32) of assistive device 10 reaches the movement limit of the mechanical or controlled movable range, control device 60 executes a cancellation process that will not respond to at least a part of the various operations for requesting executions of various actions. Specifically, if a movable section immediately after the operation of any button of operation device 50 has been completed is in the process of decelerating, even if a next button is pressed, control device 60 cancels the execution of each action requested corresponding to the button.

Further, for example, when lifting and lowering section 31 has reached the movement limit of the range of motion, that is, the mechanical or controlled lifting limit, control device 60 cancels further lifting actions and erecting actions. On the other hand, in the above example, control device 60 performs a lowering action or a seating action from the lifting end in response to a request without becoming a subject for cancellation. Control device 60 may omit the recording of an action when the action matches with the operation, and record an action when the operation does not match with the action.

The "state of the assistive device" included in log data M1 may be made to be the state of the movable section (lifting and lowering section 31, swing section 32) or the state of the action mechanism (linear motion device, a motor, etc.) in driving device 30. The state of the movable section includes, for example, the up-down position of lifting and lowering section 31 and the angle of swing section 32. These are calculated based on detection results from, for example, a linear scale provided in the linear motion device for lifting/lowering the lifting and lowering section 31, and a dedicated detection sensor 65 such as an encoder provided in the motor for rotating arm 322. The state of the action mechanism includes, for example, the current supplied to the linear motion device or the motor described above. The above current varies in accordance with the load during execution of each action.

The "state of the assistive device" included in log data M1 may be the load received from care receiver H by support member 40 supporting care receiver H. The load that support member 40 receives from care receiver H varies according to the weight and leg force of care receiver H, the posture of care receiver H, and the like. The load which support member 40 receives from care receiver H is calculated based on, for example, the detection result by a dedicated detection sensor 65 such as a load cell provided between swing main body 321 and trunk support section 41 or the current supplied to the motor to rotate swing section 32.

The "state of the assistive device" included in log data M1 may be the position of assistive device 10 at the time of executing each action. Assistive device 10 can be moved, while care receiver H is on board, to multiple positions, such as living room, bathroom, rehabilitation room, toilet room, and the like. The position of assistive device 10 is calculated, for example, based on a signal transmitted by a notification device installed at each position. The position of assistive device 10 may be calculated based on the detection result of the position from an acceleration sensor or GPS device provided in assistive device 10.

The "identification information" included in log data M1 is information for identifying care receiver H and the caregiver when assistive device 10 is used and is recorded in association with each action. When assistive device 10 is operated by care receiver H, care receiver H and the operator are recorded as being the same. The identification information may be based on, for example, detection results from a voice sensor provided in assistive device 10 and made to identify the care receiver and the caregiver when assistive device 10 is being used. The identification information may be specified based on, for example, a signal transmitted from a notification device provided on the clothing of care receiver H or the caregiver.

Log data M1 is generated and updated by control device 60 and is uploaded to management server 70 regularly or in response to a request or the like. When this occurs, log data M1 is stored in management server 70 in association with the identification information (ID) of assistive device 10.

3. Assisting a Transfer Action of Assistive Device 10

Assistive device 10 configuration as described above assists a transfer action of care receiver H. A "transfer action" is a cycle action executed in the order of erecting action and seating action. However, a transfer action does not include actions, among cycle actions, such as test runs to check the action of a movable section (lifting and lowering section 31, swing section 32) which are actions unrelated to assisting care receiver H.

In a transfer action, assistive device 10 supports a part of the body of care receiver H (e.g., the upper body of care receiver H), assists an erecting action of care receiver H in the sitting posture, and then changes direction and assists a seating action so as to re-seat care receiver H in another position. The transfer action is performed, for example, for the purpose of transferring care receiver H between a bed and a wheelchair in a living room, from a bed in a living room to a toilet seat in a toilet room, or the like.

Here, the upper end of the portion of trunk support section 41 that contacts the trunk is defined as reference position Ps. The bold line in FIG. 2 shows the movement trajectory Td of reference position Ps during execution of the erecting action and the seating action of the transfer action of care receiver H. That is, control device 60 controls the movement of support member 40 by coordinating the up-down movement of lifting and lowering section 31 and the rotation of swing section 32 so that reference position Ps moves along movement trajectory Td shown in FIG. 2.

Incidentally, in the actual transfer action, the erecting action and the seating action as described above, erecting button 51 and seating button 52 may be pressed multiple times since the caregiver always checks the posture of care receiver H and the state (position, angle) of support member 40. Further, when boarding care receiver H onto assistive device 10, after assistive device 10 is positioned with respect to care receiver H, lifting button 53 or lowering button 54 may be pressed multiple times to adjust the height of support member 40. Further, in the final stage of the transfer action, when care receiver H gets off of assistive device 10, lifting button 53 or lowering button 54 may be pressed multiple times in a similar manner to adjust the height of support member 40.

4. Configuration of Management Server 70

Management server 70 is a cloud server and is, as shown in FIG. 1, communicably connected to multiple clients (for example, multiple assistive devices 10 and multiple management devices 80) via the internet. Management server 70 stores log data M1 uploaded from multiple assistive devices 10. Further, management server 70 transmits log data M1 recorded in a predetermined assistive device 10 to management device 80 in response to a request from management device 80.

Management server 70 transmits to management device 80, for example, only a part of log data M1 relating to the predetermined assistive device 10 in response to the request. More specifically, management server 70 may be made to transmit a part of log data M1 recorded in a predetermined time period to management device 80 over the entire time period in which the predetermined assistive device 10 is operated. In addition, management server 70 may be made to transmit the information to management device 80 in a state in which some information, such as the detection value of detection sensor 65 and the identification information, is excluded. Thus, management device 80 can be made to download only necessary information from management server 70 as appropriate.

5. Configuration of Management Device 80

Management device 80 manages assistive device 10 and provides various kinds of information based on acquired log data M1. Management device 80 is, for example, a personal computer installed in a facility in which assistive device 10 is installed, a terminal device such as a portable terminal (smart phone, tablet terminal), or the like. In the present embodiment, management device 80 includes display device 81, storage device 82, analysis section 83, and calculation section 84.

Display device 81 displays various types of information generated by analysis section 83. Display device 81 may be, for example, a touch screen for accepting operations of various types of information from a viewer. Storage device 82 is configured with an optical drive device such as a hard disk drive, flash memory, or the like. Storage device 82 stores log data M1 acquired from management server 70, usage performance data M2 generated by analysis section 83, leasing conditions M3 related to the lease of assistive device 10, and billing information M4 generated by calculation section 84. Details of usage performance data M2, leasing conditions M3, and billing information M4 will be described later.

Analysis section 83 performs various analytical processes on log data M1. In the present embodiment, the analytical processes by analysis section 83 include detecting transfer actions in log data M1 and calculating the billing amount for leasing assistive device 10. Here, action history and operation history recorded in log data M1 include not only actions and operations for actually executing transfer actions but also actions and operations relating to test runs and the like while care receiver H is not on board. Therefore, analysis section 83 is configured to execute the detection of transfer actions.

In the present embodiment, analysis section 83 includes detecting section 831 and determination section 832 in order to execute the detection of transfer actions. Detecting section 831 detects cycle actions performed in the order of erecting action and then seating action in log data M1. Further, in the present embodiment, detecting section 831 detects adjustment actions executed in series in relation to at least one of an erecting action and a seating action in a cycle action. Specifically, a lifting/lowering action of support member 40 executed upon performing an erecting action and a rotating action and the like of support member 40 executed when care receiver H gets on/off may be included in adjustment actions.

Analysis section 83 sets the start action and the end action of a cycle action so as to include adjustment actions detected by detecting section 831. Thus, when a cycle action is a transfer action, the transfer action includes a series of adjustment actions. However, when any of the buttons of operation device 50 is pressed many times, it may not be easy to determine to what extent these actions are to be considered adjustment actions.

Therefore, in the present embodiment, detecting section 831 excludes, from the adjustment actions in the current cycle action, actions within a predetermined time from the end of the previous cycle action. Here, when a cycle action such as a transfer action is completed, it is conceivable to move assistive device 10 to a suitable position to perform the next cycle action or return support member 40 to the initial height for the next cycle action. Therefore, detecting section 831 processes each action executed in the predetermined time required for these operations so as not to treat the actions as adjustment actions in the current cycle action.

Further, in the present embodiment, detecting section 831 detects actions within a predetermined time from the end of the seating action in the cycle action as adjustment actions in the cycle action. Here, when the seating action in the transfer action is completed, adjusting actions such as lowering support member 40 are executed so that care receiver H is in a seated posture in which weight is deposited on a bed or a chair. Therefore, detecting section 831 processes actions executed within a predetermined time from the end of the seating action so as to treat the actions as adjustment actions.

However, detecting section 831 can change the condition as to whether each action is included in the cycle action as an adjustment action, for example, in accordance with the purpose of detecting the transfer action. For example, in the case where the purpose is to identify how assistive device 10 was used for a predetermined period of time or the cause of an action error, it is preferable to include an adjustment action executed before and after in addition to the erecting action and the seating action. On the other hand, when the purpose is to count the number of times a transfer action was performed, the cycle action does not need to include the adjustment actions.

Determination section 832 determines whether the cycle action detected by detection section 831 is a transfer action in which care receiver H is transferred based on log data M1. Since there is a possibility that trial runs and the like are included among detected cycle actions based on predetermined standards (in the present embodiment, the fact that actions are executed in the order of erecting action and then seating action), detecting section 831 determines whether a cycle action is a transfer action by various methods.

The above determination process may be performed based on the order in which each button of operation device 50 is pressed or the detection result of detection sensor 65. In the present embodiment, determination section 832 determines whether the cycle action is a transfer action based on the time relating to each action in log data M1. Specifically, determination section 832 first calculates an intermediate time, in the cycle action, from the end time of the erecting action to the start time of the seating action based on log data M1. Next, determination section 832 determines that the cycle action is a transfer action when the intermediate time is within a prescribed period.

Here, when assistive device 10 is not in a test run and assistive device 10 is loaded with care receiver H and a transfer action is executed for some purpose, a process corresponding to the purpose, such as changing direction, moving, and undressing of care receiver H, is performed after the erecting action is completed. As a result, an intermediate time equivalent to the time required for the above-mentioned process elapses. On the other hand, when the intermediate time is excessively long, for example, when the intermediate time exceeds the prescribed period, it can be determined that assistive device 10 is in a storage state. Therefore, determination section 832 determines whether the cycle action is a transfer action based on the length of the intermediate time as described above.

Further, in the case where assistive device 10 is having a test run or a transfer action is interrupted and care receiver H is returned to the initial sitting posture, the execution times, in the cycle action, of the erecting action and the seating action may be short compared with the case of a transfer action. Therefore, determination section 832 may calculate the execution time of the erecting action and the execution time of the seating action, and determine that the cycle action is a transfer action when each execution time is equal to or longer than a predetermined time.

Further, determination section 832 may determine whether the cycle action is a transfer action based on the state of assistive device 10 at the time of executing each action included in log data M1. Specifically, determination section 832, for example, in the case where the state of the action mechanism is recorded as a state of assistive device 10, the cycle action may be determined to be a transfer action when support member 40 reaches a predetermined position or a predetermined angle. Similarly, the determination may be made by the determination section 832 based on any of the recorded states of assistive device 10 (e.g., the load received by support member 40 from care receiver H, the position at which the cycle action is performed) or a combination thereof.

Analysis section 83 having the configuration as described above detects a transfer action in the acquired log data M1 and generates usage performance data M2 including at least one of the number of uses and the duration of use of assistive device 10, as shown in FIG. 4. The "number of uses" is the number of executions of a target action and is equal to, for example, the number of executions of a transfer action when a transfer action is the target. The "usage time" is the time required for a target action and is equal to, for example, the total time required for a transfer action over multiple executions when a transfer action is the target. Whether or not to include in the usage time of assistive device 10, the time not accompanied by an operation of driving device 30 can be set as appropriate.

Calculation section 84 calculates the billing amount for leasing assistive device 10 based on the number of executions of the cycle action which were determined to be transfer actions by determination section 832. Here, management device 80 of assistive system 1 of the present embodiment constitutes a charging system when assistive device 10 is lent out. The charging system is a system for performing lease charging of a leased assistive device 10. Leasing conditions M3 for each assistive device 10 or for each leasing destination is stored in storage device 82 of management device 80. Leasing conditions M3 may include, for example, information indicating the leasing period of assistive device 10, the charge per use, the conditions for changing the charge per use and the like.

In the present embodiment, calculation section 84 calculates the billing amount to the leasing destination based on usage performance data M2 generated by analysis section 83 and leasing conditions M3. Based on the billing amount included in billing information M4 generated as a result, a bill to the leasing destination is generated at the leasing source. The above-mentioned billing amount varies in accordance with the content of the usage performance data and becomes higher as the number of uses increases. For example, when a charge for one use is set as a leasing condition, the product of the number of uses and the charge per use is calculated as the billing amount. Note that the billing amount may be a fixed amount up to a prescribed number of uses depending on leasing conditions M3. The billing amount may be increased or decreased in accordance with the load on assistive device 10 and the usage time.

6. Management of Assistive Device 10 by Management Device 80

The management of assistive device 10 by management device 80 will be described with reference to FIGS. 3 to 6. The management of assistive device 10 can be executed, for example, at the discretion of a manager of assistive system 1 or as a process that is executed on a regular basis. It is assumed that log data M1 is transmitted from a predetermined assistive device 10 in advance when the management process is executed, and log data M1 including the action history and the operation history over a predetermined period of time is stored in management server 70.

As shown in FIG. 5, management device 80 first acquires log data M1 from management server 70 (S11). More specifically, identification information of assistive device 10 targeted for management is transmitted to management server 70, and one or multiple log data M1 recorded in assistive device 10 corresponding to the identification information is acquired. Next, analysis section 83 of management device 80 executes each analysis process on log data M1 in accordance with the purpose (S12). For the purpose of determining the usage state of assistive device 10 and for the purpose of calculating the billing amount, usage performance data is generated by analysis section 83.

More specifically, as shown in FIG. 6, detecting section 831 first detects a cycle action in log data M1 (detecting step, S21). Specifically, line by line in order from the current line of log data M1, detecting section 831 searches for "erecting action" under the action type heading. The above-mentioned "current line" refers to the line in log data M1 where the search starts, and the initial value is the first line (the one with the earliest start time). Next, detecting section 831 searches for "seating action" one line at a time in order from the row of log data M1 in which an erecting action is detected. Then, detecting section 831 obtains a result of whether the cycle action performed in the order of erecting action and then seating action is detected.

Determination section 832 determines whether the detected cycle action is a transfer action in which care receiver H is transferred based on log data M1 (determining step, S22 to S24). Determination section 832 first determines whether a cycle action has been detected by detection section 831 (S22). When a cycle action is detected (S22: Yes), determination section 832 calculates intermediate time Tm, in the cycle action, from the end time of the erecting action to the start time of the seating action (S23). Next, determination section 832 determines whether intermediate time Tm is within a prescribed time period (Lt–Mt) (S24).

When intermediate time Tm is not within prescribed time period (Lt-Mt) (S24: No), determination section 832 determines that the cycle action is not a transfer action. Then, detecting section 831 sets a row next to the row in which the seating action in the above-described cycle action is recorded in the action history as the current row, and restarts the detection of cycle actions in log data M1 (S21). On the other hand, when intermediate time Tm is within the prescribed time period (Lt–Mt) (S24: Yes), determination section 832 determines that the cycle action is a transfer action.

At this stage, the start action and the end action of the cycle action determined to be a transfer action as described above are yet to be set. Detecting section 831 includes as appropriate, in the cycle action, adjustment actions of the erecting action and adjustment actions of the seating action in accordance with the purpose of detecting transfer actions. Thus, analysis section 83 sets the start action and the end action of the cycle action. Depending on the purpose of detecting the transfer action, the adjustment actions may be omitted. In this case, the erecting action is set as the start action of the transfer action, and the seating action is set as the end action of the transfer action.

In this embodiment, detecting section 831 includes in the cycle action, adjustment actions performed in series associated with the erecting action in the transfer action (S25). "Adjustment actions performed in series" are multiple actions performed continuously, and refers to actions in which the pause time of the driving device 30 is within a predetermined time (e.g., 10 seconds). Detecting section 831 detects actions executed in series before the start time of the erecting action and sets the actions as adjustment actions. In this case, even if the actions are executed in series with the erecting action, detecting section 831 excludes, the actions that are within a predetermined time Ct1 from the end of the previous cycle action, from the adjustment actions in the current cycle action.

Detecting section 831 includes in the cycle action, adjustment actions performed in series in connection with the seating action in transfer action (S26). Detecting section 831 detects a series of actions performed after the end time of the seating action and sets the actions as adjustment actions. At this time, detecting section 831 sets actions within a predetermined time Ct2 from the end of the seating action as adjustment actions in a cycle action. That is, even if the action is performed in series with the seating action, detecting section 831 does not include in the cycle action, actions that are performed after the predetermined period of Ct2 has elapsed from the end of the seating action.

Analysis section 83 sets the start action and end action of the cycle action that is determined to be a transfer action, by detecting adjustment actions as described above (S25, S26). Analysis section 83 then updates usage performance data M2 based on the current transfer action (S27). Specifically, when a transfer action is detected, the number of times assistive device 10 is used is counted, and the time required for a transfer action (the difference between the start time of the start action and the end time of the end action) is added as usage time.

Detecting section 831 restarts detection of cycle actions in log data M1, with the current line being the line following the line in which the end action, in the cycle action determined to be a transfer action, was recorded as action history (S21). In this manner, the cycle action detecting step (S21), the determining step for determining whether the cycle action is a transfer action (S22-S24), the setting of adjustment actions related to the cycle action (S25, S26), and the updating of usage performance data M2 (S27) are repeated toward the last row of log data M1. When a cycle action is not detected (S22: No), analysis section 83 ends the analysis process.

When the analysis process (S12) by analysis section 83 is completed, calculation section 84 calculates the billing amount relating to the lease of assistive device 10 (S13). More specifically, calculation section 84 calculates, as the billing amount, an amount obtained by multiplying the number of uses (i.e., the number of executions of the transfer action) of assistive device 10 in usage performance data M2 generated in the analysis process (S12) by the charge per use prescribed in leasing conditions M3, and generates billing information M4.

In addition to the purpose of generating billing information M4 as described above, management device 80 may use usage performance data M2, for example, for making effective use of assistive device 10 or, together with log data M1, identifying causes for errors of assistive device 10 when such errors occur. Management device 80 causes display device 81 to display billing information M4 generated by calculation section 84. When this occurs, management device 80 may display usage performance data M2 and leasing conditions M3 in addition to billing information M4.

7. Effects Provided by the Configuration of the Embodiment

Management device 80 of assistive device 10 of the present embodiment is used for assistive device 10 which assists the erecting action and the seating action of care receiver H and records the action history including the erecting action and the seating action as log data M1. Management device 80 includes detecting section 831 for detecting a cycle action executed in the order of the erecting action and the seating action in log data M1, and determination section 832 for determining based on log data M1 whether the detected cycle action is a transfer action in which care receiver H is transferred.

With such a configuration, since it is determined whether the cycle action in log data M1 is a transfer action, it is possible to more accurately detect the transfer action in log data M1. As a result, it is possible to improve the accuracy of analysis using log data M1, such as calculation of the number of times assistive device 10 is used and the duration of use.

8. Variation of the Embodiment

In the embodiment, management device 80 acquires log data M1 recorded by assistive device 10 via management server 70. In contrast to this, management device 80 may acquire log data M1 by directly communicating with assistive device 10, for example. Further, management device 80 may be configured to be partially incorporated in management device 80. More specifically, management device 80 may incorporate analysis section 83 and calculation section 84 into management server 70 and transmit the results of the analysis to a terminal device owned by the user of assistive device 10.

In the embodiment, base 20 of assistive device 10 to be managed by management device 80 includes footrest 23 on which both feet of care receiver H are placed. In assistive device 10 such as this, a portion of the weight of care receiver H is received by footrest 23 while the upper body of care receiver H is supported by support member 40. As a result, assistive device 10 allows care receiver H who does not have the leg force necessary for the erecting action or walking to move on the vehicle. In contrast to this, the assistive device may be, for example, one that does not have footrest 23, supports a portion of the weight of care receiver H when care receiver H moves using his/her own feet, and assists the walking action of care receiver H. Management device 80 exhibits the same effect as that of the embodiment even when such a type of assistive device is to be managed.

The invention claimed is:
1. An assistive system, comprising:
an assistive device configured to assist an erecting action and a seating action of a care receiver; the assistive device comprising:
a memory, storing an action history including erecting actions and seating actions as a log data,
a base;
a support member configured to be moveable relative to the base, the support member is adapted to support the care receiver;
a motor, assisting at least one of the erecting action or the seating action;
an operation device, comprising:
a first button, to initiate the erecting action;
a second button, to initiate the seating action;

a management device, comprising a processor configured to function as:
- a detecting section configured to detect, in the log data, a plurality of cycle actions, each cycle action is identified by executing in consecutive order the erecting action and then the seating action, the plurality of cycle actions includes a cycle action that is a transfer action in which the care receiver was transferred and a cycle action that is a non transfer action in which the care receiver was not transferred; and
- a determination section configured to determine, based on the log data, whether each cycle action detected is the transfer action or the non transfer action.

2. The assistive system of claim 1, wherein the log data includes a start time and an end time for each action including the erecting action and the seating action, and the determination section determines whether the cycle action is a transfer action based on a time related to each action in the log data.

3. The assistive system of claim 2, wherein the determination section calculates, in the cycle action, an intermediate time period from the end time of the erecting action to the start time of the seating action based on the log data, and determines that the cycle action is a transfer action when the intermediate time period falls within a prescribed period.

4. The assistive system of claim 2, wherein the determination section calculates an execution time, in the cycle action, of the erecting action and the seating action based on the log data, and determines that the cycle action is a transfer action when each of the execution times is equal to or longer than a predetermined time.

5. The assistive system of claim 1, wherein the log data includes a state of the assistive device at a time of executing each action including the erecting action and the seating action, and the determination section determines whether the cycle action is a transfer action based on the state of the assistive device at the time of executing each action included in the log data.

6. The assistive system of claim 5, wherein the state of the assistive device includes at least one piece of data of: a position or an angle of a movable section in the assistive device, a value of a current supplied to a driving device configured to operate the movable section, a load received from the care receiver by a support member configured to support the care receiver, and a position of the assistive device when each action is performed.

7. The assistive system of claim 1, wherein the detecting section detects adjustment actions executed in series related to at least one of the erecting action or the seating action in the cycle action, and the management device sets a start action and an end action of the cycle action so that the adjustment actions detected are included.

8. The assistive system of claim 7, wherein the detection section excludes, from the adjustment actions in the current cycle action, actions within a predetermined time from an end of the previous cycle action.

9. The assistive system of claim 7, wherein the detecting section detects actions within a predetermined time from the end of the seating action in the cycle action as adjustment actions in the cycle action.

10. The assistive system of claim 1, wherein the management device includes a billing system when the assistive device is lent, and the management device further comprises a calculation section configured to calculate a billing amount related to the lease of the assistive device based on a number of executions in which a cycle action was determined to be a transfer action by the determination section.

11. A management method for an assistive device configured to assist an erecting action and a seating action of a care receiver, the assistive device comprising:
- a memory, storing an action history including erecting actions and seating actions as a log data;
- a base;
- a support member configured to be moveable relative to the base, the support member is adapted to support the care receiver;
- a motor, assisting at least one of the erecting action or the seating action;
- an operation device, comprising:
  - a first button, to initiate the erecting action;
  - a second button, to initiate the seating action:

the management method comprising:
- a detecting step for detecting, in the log data, a plurality of cycle actions, each cycle action is identified by executing in consecutive order the erecting action and then the seating action, the plurality of cycle actions includes a cycle action that is a transfer action in which the care receiver was transferred and a cycle action that is a non transfer action in which the care receiver was not transferred; and
- a determining step for determining, based on the log data, whether each cycle action detected is the transfer action or the non transfer action.

* * * * *